(12) United States Patent
Iwasaki et al.

(10) Patent No.: US 6,346,402 B1
(45) Date of Patent: Feb. 12, 2002

(54) (S)-α-PHENETHYLAMINE: PYRUVATE TRANSAMINASE

(75) Inventors: Akira Iwasaki; Yukio Yamada, both of Kakogawa; Yasuhiro Ikenaka, Kobe; Yoshihiko Yasohara, Himeji; Junzo Hasegawa, Akashi, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/582,764
(22) PCT Filed: Oct. 29, 1999
(86) PCT No.: PCT/JP99/05997
  § 371 Date: Jun. 30, 2000
  § 102(e) Date: Jun. 30, 2000
(87) PCT Pub. No.: WO00/26351
  PCT Pub. Date: May 11, 2000

(30) Foreign Application Priority Data

Oct. 30, 1998 (JP) .............................. 10-309310

(51) Int. Cl.$^7$ ................................. C12P 13/04
(52) U.S. Cl. ................. 435/106; 435/41; 435/183; 435/243
(58) Field of Search ................. 435/106, 41, 183, 435/243

(56) References Cited

U.S. PATENT DOCUMENTS 4,950,606 A    8/1990   Stirling et al.

FOREIGN PATENT DOCUMENTS

| JP | A2227073 | 9/1990 |
| JP | A6178685 | 6/1994 |

OTHER PUBLICATIONS

Partial English Translation of Japanese Patent Laid–Open No. Hei 1–174398 (Jul. 10, 1989) with corresponding portions of Japanese publication.

English Abstract and Partial English Translation of Japanese Patent Laid–Open No. Hei 6–253891 (Sep. 13, 1994) with corresponding portions of Japanese publication.

Partial English Translation of Japanese Patent Laid–Open No. Hei 4–365490 (Dec. 17, 1992) with corresponding portions of Japanese publication.

English Abstract and Partial English Translation of Japanese Patent Laid–Open No. 6–253875 (Sep. 13, 1994) with corresponding portions of Japanese publication.

Partial English Translation of Japanese Patent Laid–Open No. Sho 63–273486 (Nov. 10, 1988) with corresponding portions of Japanese Publication.

Partial English Translation of Japanese Examined Patent Publication No. Hei 4–11194 (Feb. 27, 1992) with corresponding portions of Japanese publication.

*Primary Examiner*—Leon B. Lankford, Jr.
*Assistant Examiner*—Brett Ozga
(74) *Attorney, Agent, or Firm*—Birch, Stewart, Kolasch & Birch, LLP

(57) ABSTRACT

Relating to an enzyme capable of efficiently converting a ketone compound to an optically active amino compound by transamination, and a process for preparing an optically active amino compound using the enzyme. An (S)-α-phenethylamine:pyruvate transaminase, which acts on (S)-α-phenethylamine and a ketone compound, thereby catalyzing transamination for forming acetophenone and an amino compound corresponding to the ketone compound; a process for preparing an optically active amino compound using the transaminase; and a method for culturing a microorganism for producing the above transaminase, comprising adding to a medium one or more compounds selected from the group consisting of propylamine, 1-butylamine, 2-butylamine, 2-pentylamine, isopropylamine and isobutylamine as an inducer for the enzyme when a microorganism for producing (S)-α-phenethylamine:pyruvate transaminase is cultured.

24 Claims, 3 Drawing Sheets

F I G. 1
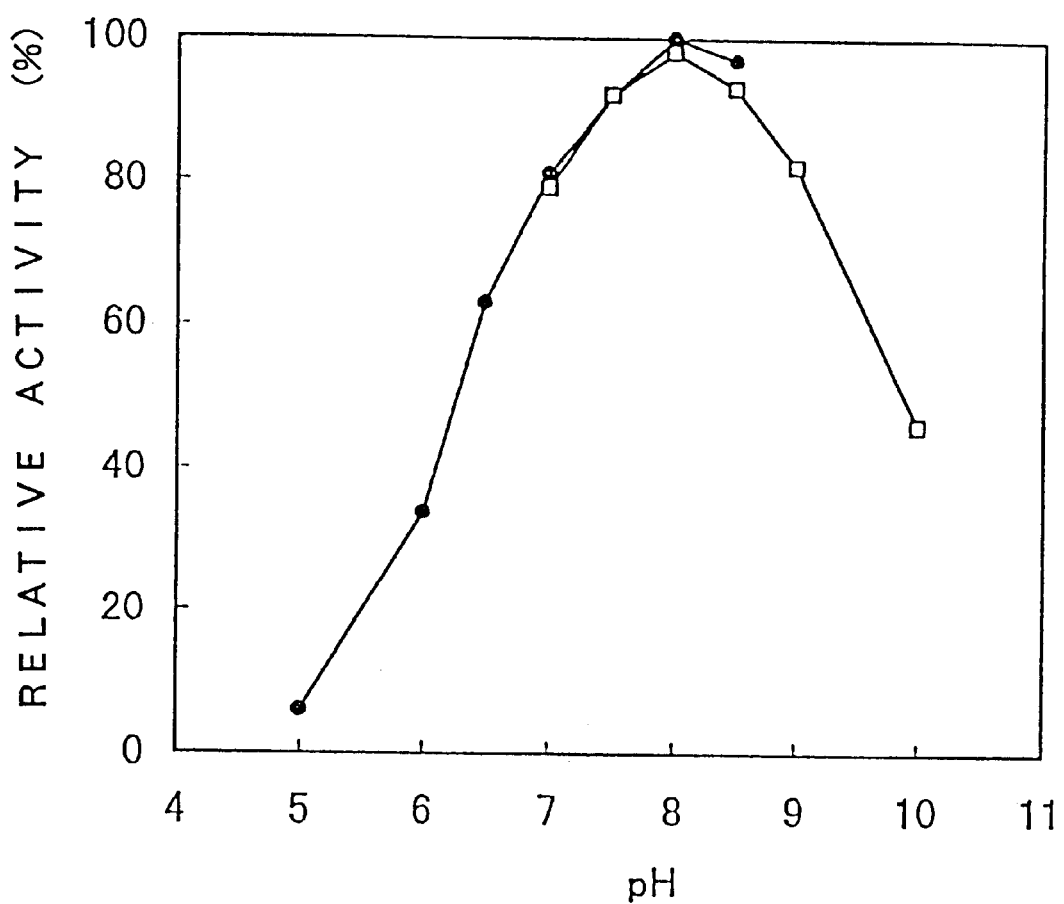

SEQUENCE LISTING

<160> NUMBER OF SEQ ID NOS: 1

<210> SEQ ID NO 1
<211> LENGTH: 16
<212> TYPE: PRT
<213> ORGANISM: Pseudomonas sp.

<400> SEQUENCE: 1

```
Met Tyr Glu Gln Tyr Lys Thr Ala Gln Lys Lys Phe Trp His Pro Met
1               5                   10                  15
```

(S)-α-PHENETHYLAMINE: PYRUVATE TRANSAMINASE

This application is the national phase under 35 U.S.C. § 371 of PCT International Application No. PCT/JP99/05997 which has an International filing date of Oct. 29, 1999, which designated the United States of America.

TECHNICAL FIELD

The present invention relates to an enzyme capable of efficiently converting a ketone compound to an optically active amino compound by transamination, and a process for preparing an optically active amino compound using the enzyme. The resulting optically active amino compound can be utilized as an intermediate for pharmaceuticals and agricultural chemicals.

BACKGROUND ART

As a process for biochemically preparing optically active amino compounds, there have been known processes for preparing optically active α-phenethylamine by a method of asymmetric degradation of racemic α-phenethylamine by a microorganism (Japanese Patent Laid-Open Nos. Hei 1-174398 and Hei 6-253891); by a method for aminating acetophenone by a microorganism (Japanese Patent Laid-Open Nos. Hei 4-365490 and Hei 6-253875), and the like. However, in these processes, the properties of the enzyme participating in the reaction, for instance, dehydrogenase, oxidase, ammonia-lyase, and the like, are not shown. Further, since the productivity of the optically active amino compounds by the above processes is also low, it would be thought that its practical use on an industrial scale is difficult. Also, these processes do not describe on the preparation of the optically active amino compounds other than α-phenethylamine.

On the other hand, there has been reported that optically active 1-(4-methoxyphenyl)-2-aminopropane can be synthesized by subjecting 1-(4-methoxyphenyl)-2-propanone to transamination using a microorganism belonging to the genus Brevibacterium (Japanese Patent Laid-Open No. Sho 63-273486). The above publication discloses that there is an effect of adding a reduced coenzyme, for instance, nicotinamide adenine dinucleotide, in the reaction. From the above, the enzyme utilized is thought to be dehydrogenase, but it is not actually clear.

In addition, Japanese Examined Patent Publication No. Hei 4-11194 discloses that a microorganism belonging to the genus Brevibacterium produces (R)-1-(4-methoxyphenyl)-2-aminopropane from 1-(4-methoxyphenyl)-2-propanone in the presence of ammonium chloride. The present inventors have conducted an additional study on the microorganism and the substrate disclosed in the above publication, and as a result, they were found to be extremely poor in the reproducibility.

Further, Japanese Patent Laid-Open No. Hei 3-103192 discloses that an ω-amino acid transaminase is allowed to act on a racemic amino compound, to degrade only an (S) modification, thereby obtaining the remaining (R) modification. In the above publication, since the reaction of the transaminase is inhibited by a transaminase inhibitor such as gabaculine or hydroxylamine, the enzyme used is considered to be an ω-amino acid transaminase. However, it would be insufficient to specify an enzyme simply from the action of the inhibitor, and moreover, the reactivity of the enzyme used for the ω-amino acid is not disclosed. Also, according to this process, the amino compound having an opposite optical activity to a desired compound is undesirably degraded in order to obtain an optically active amino compound, as in the case of a process of asymmetrically degrading a microorganism (Japanese Patent Laid-Open Nos. Hei 1-174398 and Hei 6-253891). Therefore, there is a defect that the yield for the substrate is lowered to 50% or less, making it disadvantageous in costs.

DISCLOSURE OF INVENTION

An object of the present invention is to provide an enzyme capable of efficiently converting a ketone compound to an optically active amino compound by transamination; a process for preparing an optically active amino compound using the enzyme; and a method for culturing a microorganism producing the above enzyme.

As a result of screening from various soils, the present inventors have been able to obtain a microorganism having (S)-α-phenethylamine:pyruvate transaminase activity, the transaminase activity capable of converting (S)-α-phenethylamine to acetophenone in the presence of pyruvic acid, and able to isolate and purify the enzyme having the activity from the microorganism. Further, as a result of a detailed study on the reaction characteristics of the (S)-α-phenethylamine:pyruvate transaminase, the present inventors have found that the enzyme has excellent characteristics of allowing to act not only to an α-keto acid but also to a ketone compound other than the α-keto acid by using (S)-α-phenethylamine or the like as an amino group donor, converting them to a corresponding optically active amino compound, and the present invention has been accomplished thereby.

The gist of the present invention relates to:

[1] an (S)-α-phenethylamine:pyruvate transaminase having the following physicochemical properties:
(A) action:
acting on optically active (S)-α-phenethylamine and pyruvic acid, thereby catalyzing transamination for forming acetophenone and alanine, respectively; and
(B) substrate specificity:
(a) amino group donor: exhibiting activity to (S)-α-phenethylamine but not exhibiting activity to each of β-alanine, taurine, putrescine, DL-ornithine and DL-lysine; and
(b) amino group receptor: exhibiting activity to pyruvic acid and glyoxylic acid;

[2] a process for preparing an optically active amino compound, characterized in that the process comprises acting the (S)-α-phenethylamine:pyruvate transaminase of item [1] above on a ketone compound represented by the following general formula (1):

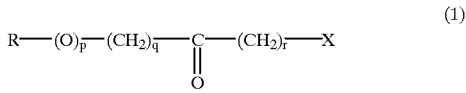

(1)

wherein p is 0 or 1; q is an integer of 0 to 8; r is an integer of 0 to 4; R is a substituted or unsubstituted aryl group having 6 to 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkoxycarbonyl group having 2 to 6 carbon atoms, or hydrogen atom, in the presence of an amino group donor, to thereby give an optically active amino compound having the configuration represented by the general formula (2):

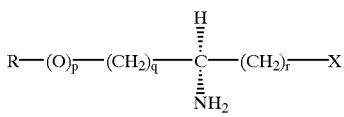

(2)

wherein each of p, q, r, R and X has the same definitions as those of p, q, r, R and X in the general formula (1);

[3] a process for preparing an optically active amino compound, characterized in that the process comprises acting the (S)-α-phenethylamine:pyruvate transaminase of item [1] on a racemic modification of an amino compound represented by the general formula (4):

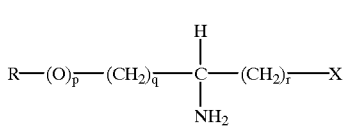

(4)

wherein p is 0 or 1; q is an integer of 0 to 8; r is an integer of 0 to 4; R is a substituted or unsubstituted aryl group having 6 to 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkoxycarbonyl group having 2 to 6 carbon atoms, or hydrogen atom, in the presence of an amino group receptor, to thereby give an optically active amino compound having the configuration represented by the general formula (5):

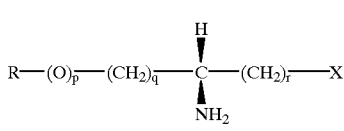

(5)

wherein each of p, q, r, R and X has the same groups as those of p, q, r, R and X in the general formula (4); and

[4] a method for culturing a microorganism for producing (S)-α-phenethylamine:pyruvate transaminase, comprising adding to a medium one or more compounds selected from the group consisting of propylamine, 1-butylamine, 2-butylamine, 2-pentylamine, isopropylamine and isobutylamine as an inducer for the enzyme when the microorganism for producing (S)-α-phenethylamine:pyruvate transaminase is cultured.

BRIEF DESCRIPTION OF THE DRAWINGS

FIG. 1 is a graph showing an optimal pH of (S)-α-phenethylamine:pyruvate transaminase. In the figure, solid circles indicate the assay results when using 0.1M phosphate buffer, and open circles indicate the assay results when using 0.1M Tris-hydrochloric acid buffer.

BEST MODE FOR CARRYING OUT THE INVENTION

Figure 2:
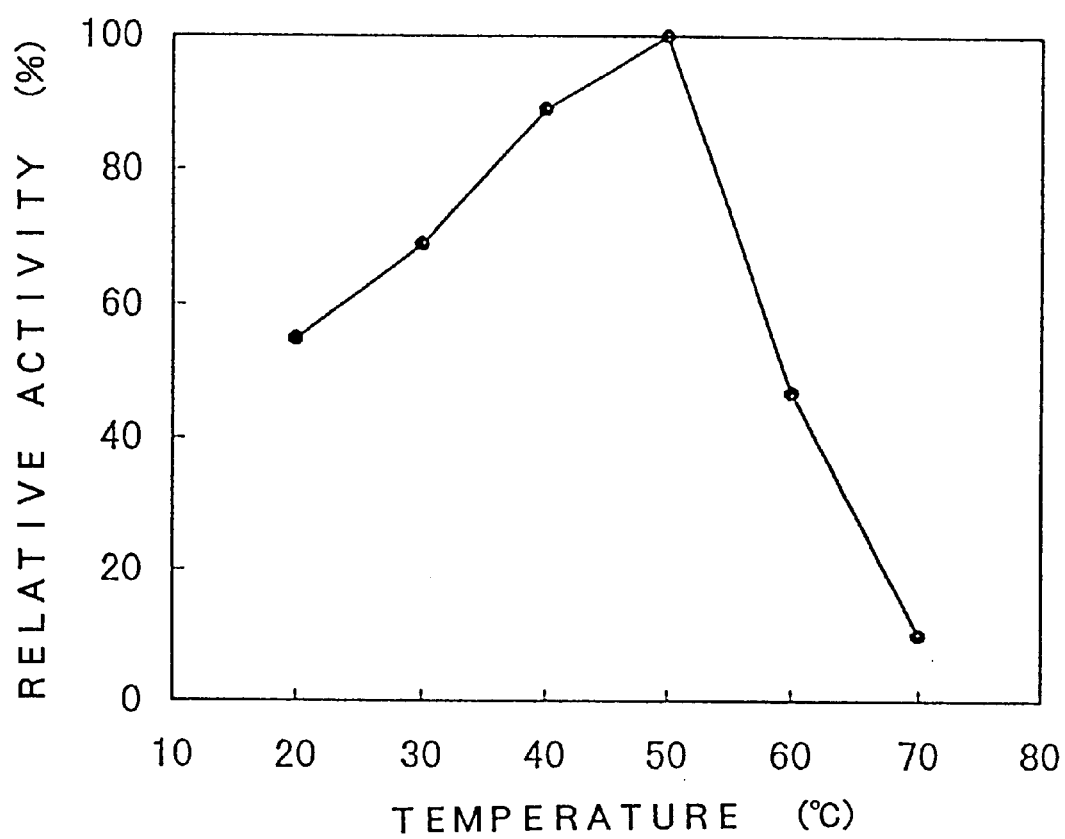
FIG. 2 is a graph showing an optimal temperature of (S)-α-phenethylamine:pyruvate transaminase.

The (S)-α-phenethylamine:pyruvate transaminase of the present invention is an enzyme having the following physicochemical properties:

(A) action:
  acting on optically active (S)-α-phenethylamine and pyruvic acid, thereby catalyzing transamination for forming acetophenone and alanine, respectively; and
(B) substrate specificity:
  (a) amino group donor: exhibiting activity to (S)-α-phenethylamine but not exhibiting activity to each of β-alanine, taurine, putrescine, DL-ornithine and DL-lysine; and
  (c) amino group receptor: exhibiting activity to pyruvic acid and glyoxylic acid.

Further, the enzyme of the present invention can act on (S)-α-phenethylamine and on a ketone compound other than an α-keto acid, thereby making to catalyze transamination for forming acetophenone and an amino compound corresponding to the ketone compound.

Since the enzyme of the present invention has the substrate specificity as mentioned above and catalyzes transamination stereoselectively, an optically active amino compound can be obtained by the use of the present enzyme in a higher yield and more easily than the prior art.

Further, the enzyme of the present invention may have the following physicochemical properties:
  a) molecular weight: about 44,000 (SDS-PAGE);
  b) optimal pH: 7.0 to 9.0;
  c) optimal temperature: 30° to 50° C.; and
  d) thermostability: retaining a remaining activity of 95% or more of a total activity before treatment, when treated at pH 7.0 and a temperature of 30° to 50° C. for 15 minutes.

The above "ketone compound" includes a ketone compound represented by the general formula (1):

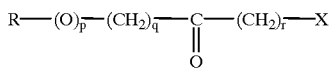

(1)

wherein p is 0 or 1; q is an integer of 0 to 8; r is an integer of 0 to 4; R is a substituted or unsubstituted aryl group having 6 to 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkoxycarbonyl group having 2 to 6 carbon atoms or hydrogen atom. The ketone compound includes, for instance, 3-methoxyacetophenone, 2-hydroxyacetophenone, 3-hydroxyacetophenone, 4-chloroacetophenone, 4'-methoxyacetophenone, 3',4'-dimethoxyphenyl acetone, 3'-trifluoromethyl acetone, benzyl acetone, 4-(4'-methoxyphenyl)-2-butanone, benzoyl acetone, 2-acetylpyridine, 3-acetylpyridine, 4-acetylpyridine, acetylpyrazine, 2-acetylfuran, 2-acetylthiazole, and the like. However, one of the features of the enzyme of the present invention also resides in that the enzyme does not act on 2-ketoglutaric acid.

In the above general formula (1), p is 0 or 1; q is an integer of 0 to 8, preferably 0 to 4; and r is an integer of 0 to 4, preferably 0 to 2.

In the above general formula (1), R is a substituted or unsubstituted aryl group having 6 to 14 carbon atoms, preferably 6 to 10 carbon atoms; a heterocyclic group having 4 to 12 carbon atoms, preferably 4 to 8 carbon atoms; carboxyl group; an alkoxycarbonyl group having 2 to 6 carbon atoms, preferably 2 to 4 carbon atoms; methyl group; or hydrogen atom.

The above substituted aryl group includes, for instance, an aryl group substituted in at least one site by a substituent selected from the group consisting of a halogen atom, an alkyl group having 1 to 6 carbon atoms, preferably 1 to 4 carbon atoms, hydroxyl group, methoxy group, nitro group, monofluoromethyl group, difluoromethyl group and trifluoromethyl group.

Concrete examples of R include methyl group, phenyl group, naphthyl group, 2-chlorophenyl group, 3-chlorophenyl group, 4-chlorophenyl group, 2-hydroxyphenyl group, 3-hydroxyphenyl group, 4-hydroxyphenyl group, 2-methoxyphenyl group, 3-methoxyphenyl group, 4-methoxyphenyl group, 2,4-dimethoxyphenyl group, 3,4-dimethoxyphenyl group, 2-trifluoromethylphenyl group, 3-trifluoromethylphenyl group, 4-trifluoromethylphenyl group, pyridyl group, pyrazinyl group, pyrrolyl group, thienyl group, furyl group, thiazolyl group, and the like.

In the above general formula (1), X is hydroxyl group, carboxyl group, an alkoxycarbonyl group having 2 to 6 carbon atoms, preferably 2 to 4 carbon atoms, or hydrogen atom.

The enzyme of the present invention can act on (S)-α-phenethylamine and 3-hydroxyacetophenone, thereby making to form acetophenone and an optically active (S)-3-α-hydroxy-phenethylamine.

The enzyme is present in a microorganism of the genus Pseudomonas, or the like. Among them, the representative Pseudomonas species is named and indicated as Pseudomonas sp. KNK425, and deposited with an accession number FERM BP-6525 with National Institute of Bioscience and Human-Technology, Agency of Industrial Science and Technology [address: 1–3, Higashi 1-chome, Tsukuba-shi, Ibaraki-ken, Japan (zip code: 305-8566)], since Sep. 25; 1998 (date of original deposit). The bacteriological natures of Pseudomonas sp. KNK425 (hereinafter simply referred to as "KNK425 strain" in some cases) are shown as follows.

| Bacteriological Nature | |
| --- | --- |
| Cell Morphology: | Rod |
| Gram Staining: | Negative |
| Spore Formation: | None |
| Mobility: | Some |
| Colony Morphology: | Colony with round, regular, entire, yellow, smooth, glossy, flat, semi-translucent, 3 mm in diameter (yeast-glucose agar medium) |
| Growth (37° C.): | + |
| (41° C.): | − |
| Catalase: | + |
| Oxidase: | + |
| OF Test (glucose): | − |

The enzyme derived from the above KNK425 strain can be, for instance, purified as follows:

First, Pseudomonas species KNK425 is inoculated to a 50 mL medium [composition: 5 g/L $KH_2PO_4$, 5 g/L $K_2HPO_4$, 1 g/L $MgSO_4.7H_2O$, 0.005 g/L $ZnSO_4.7H_2O$, 0.005 g/L $FeSO_4.7H_2O$, 0.001 g/L $MnCl_2.4H_2O$, 3 g/L NaCl, 15 g/L glycerol, 2 g/L yeast extract, 8 g/L proextract, 2 g/L (RS)-2-butylamine, 1.5 g/L pyruvic acid (pH 7.2)] in a 500-mL Sakaguchi flask, and cultured at 30° C. for 1 day, to give a preculture. Subsequently, the resulting preculture is inoculated to a 3.0-liter medium (the same composition as the medium mentioned above) in a 5-liter mini jar, and cultured at 30° C. for 22 hours under conditions of 0.5 vvm, 600 rpm and a pH of 7.5 or less.

Incidentally, when the above microorganism is cultured, the microorganism can be also added to a medium propylamine, 1-butylamine, 2-butylamine, 2-pentylamine, isopropylamine, isobutylamine or the like as an inducer for (S)-α-phenethylamine:pyruvate transaminase. The above inducer may be used alone or in admixture of two or more kinds.

The amount of the above inducer added is not particularly limited, and it is preferable that the amount is usually 1% by weight or less of the medium composition, from the viewpoint of inhibition of growth of bacterial cells, and the like.

In addition, the timing of addition of the above inducer is not particularly limited, and the inducer may be added at initiation of culture or during culturing.

Subsequently, the bacterial cells are harvested from the resulting culture by centrifugation, and the cells are suspended in 0.05 M potassium phosphate buffer (pH 6.8) containing 0.1% 2-mercaptoethanol and 0.1 mM pyridoxal phosphate.

The resulting suspension is disrupted by DYNOMILL, and thereafter supernatant is obtained by centrifugation. The resulting supernatant is heat-treated at 50° C. for 30 minutes, and thereafter the precipitates are removed by centrifugation. Sulfate protamine is added to the resulting supernatant, to remove a nucleic acid.

The resulting sulfate protamine-treated solution can be further purified by various chromatographies representatively exemplified by ion exchange chromatography, adsorption chromatography, hydrophobic chromatography, and the like. It is preferable that the operation of each of various chromatographies is carried out at 5° to 10° C.

Preferably, the resulting sulfate protamine-treated solution is charged to DEAE-Sepharose Fast Flow (Pharmacia LKB) column, and eluted on a 0–0.2 M NaCl linear concentration gradient, to collect an active fraction. The resulting active fraction is charged to Q-Sepharose (Pharmacia LKB) column, and eluted on a 0–0.25M NaCl linear concentration gradient, to collect an active fraction. The resulting active fraction is charged to Phenyl-Sepharose Fast Flow column, and eluted on a stepwise concentration gradient of 5%, 10% and 30% ethylene glycol, to collect an active fraction. This active fraction shows almost a single band by SDS-polyacrylamide gel electrophoresis.

The assay for the (S)-α-phenethylamine:pyruvate transaminase activity in the present invention is as follows.

To 0.9 mL of 0.1M potassium phosphate solution (pH 7.0) having the following composition is added 0.1mL of the enzyme preparation. The mixture is reacted at 30° C. for 1 hour, and thereafter 0.1 mL of 1N HCl is added thereto. The formed acetophenone is quantified by high-performance liquid chromatography.

| Composition | |
| --- | --- |
| (S)-α-Phenethylamine | 22.5 mM |
| Pyruvic Acid | 22.5 mM |
| Pyridoxal Phosphate | 0.1 mM |

The assay conditions by high-performance liquid chromatography are as follows.

| | |
| --- | --- |
| Column: | Deverosil ODS-HG-3 (NOMURA CHEMICAL) |
| Eluent: | 750 mL of acetonitrile/2250 mL of distilled water/6.75 g of $KH_2PO_4$/2.7 g of $H_3PO_4$ |
| Flow Rate: | 1 mL/minute |
| Detection: | 210 nm |

Here, the value for the enzyme activity is such that an amount of the enzyme for producing 1 μmol of acetophenone in 1 minute is defined as 1 unit.

In the purified enzyme as described above, information on its partial amino acid sequence can be obtained by a conventional technique. Concretely, N-terminal amino acid sequence can be determined by directly sequencing the amino acid sequence of the purified enzyme by means of Edman degradation method using a vapor phase protein-sequencer [492 PROTEIN SEQUENCER (manufactured by Applied Biosystems)] or the like. The enzyme obtained in the manner described above includes, for instance, an enzyme having the amino acid sequence as shown in SEQ ID NO: 1 as N-terminal amino acid sequence, and the like. Such an enzyme is also encompassed in the present invention.

As to the substrate specificity for the amino group donor, when (S)-α-phenethylamine is used, the enzyme of the present invention exhibits high activity, and as to the substrate specificity for the amino group receptor, when pyruvic acid and glyoxylic acid are used, the enzyme of the present invention exhibits activity. The enzyme of the present invention is characterized as (S)-α-phenethylamine:pyruvate transaminase from these properties.

As shown in Table 1 given below, since the (S)-α-phenethylamine:pyruvate transaminase of the present invention does not act on each of glycine, DL-ornithine, DL-lysine, L-aspartic acid and DL-glutamic acid, it is suggested that the (S)-α-phenethylamine:pyruvate transaminase is not the conventionally known α-amino acid transaminase. In addition, since the (S)-α-phenethylamine:pyruvate transaminase of the present invention does not also act on an inorganic ammonium salt such as ammonium chloride, it is suggested that it is different from the enzyme derived from Brevibacterium as disclosed in Japanese Examined Patent Publication No. Hei 4-11194.

TABLE 1

| Amino Group Donor | Amino Group Receptor | Relative Activity (%) |
| --- | --- | --- |
| (S)-α-Phenethylamine | Pyruvic Acid | 100 |
| Ammonium Chloride | Pyruvic Acid | 0 |
| Glycine | Pyruvic Acid | 0 |
| DL-Ornithine | Pyruvic Acid | 0 |
| DL-Lysine | Pyruvic Acid | 0 |
| L-Aspartic Acid | Pyruvic Acid | 0 |
| DL-Glutamic Acid | Pyruvic Acid | 0 |

In addition, to the substrate of a representative ω-amino acid transaminase, the reactivity of the (S)-α-phenethylamine:pyruvate transaminase of the present invention is compared with the reactivity of a conventionally known, representative ω-amino acid transaminase. As a result, the enzyme of the present invention does not act on a substrate for a representative ω-amino acid transaminase such as β-alanine, taurine, putrescine or 4-aminobutyric acid, but specifically exhibits high activity to (S)-α-phenethylamine. Therefore, it is shown that the present enzyme is different from the conventional ω-amino acid transaminase, and the enzyme is also clearly different from the enzyme used in Japanese Patent Laid-Open No. Hei 3-103192.

Here, the term "representative ω-amino acid transaminase" refers to ω-amino acid:pyruvate transaminase derived from the genus Pseudomonas bacteria F-126 described in *Agric. Biol. Chem.* 41, 1701(1977); and 4-aminobutyrate:2-ketoglutarate transaminase derived from the genus Pseudomonas bacteria F-126 described in *Arch. Biochem. Biophys.* 200, 156.

From the above aspects, it is suggested that the (S)-α-phenethylamine:pyruvate transaminase of the present invention is a novel enzyme completely different from the conventionally known transaminase. Further, the (S)-α-phenethylamine:pyruvate transaminase of the present invention has an ability of catalyzing the reaction of converting to corresponding optically active amino compounds not only an α-keto acid such as pyruvic acid but also various ketone compounds other than α-keto acid as an amino group receptor.

A process for preparing an optically active amino compound is provided by the (S)-α-phenethylamine:pyruvate transaminase of the present invention. Such a process for preparing an optically active amino compound is encompassed in the present invention.

One of the great features of the process for preparing an optically active amino compound of the present invention resides in the use of the enzyme of the present invention. In the present invention, since the enzyme is used, the optically active amino compound can be prepared at a high efficiency on the basis of the stereoselectivity owned by the enzyme.

The process for preparing an optically active amino compound of the present invention includes a process of using an amino group donor as a substrate (hereinafter referred to as "Process I"); and a process of using an amino acid receptor by utilizing a reverse reaction (hereinafter referred to as "Process II").

Process I

The (S)-α-phenethylamine:pyruvate transaminase of the present invention acts on a ketone compound represented by the general formula

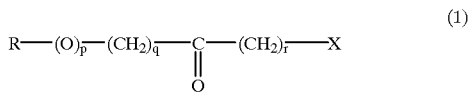

(1)

in the presence of an amino group donor such as (S)-α-phenethylamine, to thereby give an optically active amino compound having the configuration represented by the general formula (2):

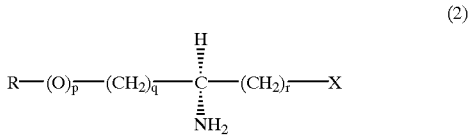

(2)

Among the above ketone compounds represented by the general formula (1), preferable is a compound where p is 0, q is 0, r is 1 and X is hydrogen atom or where p is 0, q is 1, r is 1 and X is hydrogen atom. Further, concrete examples thereof include 4-chloroacetophenone, 2-hydroxyacetophenone, 3-hydroxyacetophenone, 4-hydroxyacetophenone, 2-methoxyacetophenone, 3-methoxyacetophenone, 4-methoxyacetophenone, 2,4-dimethoxyacetophenone, 3,4-dimethoxyacetophenone, 2-trifluoromethylacetophenone, 3-trifluoromethylacetophenone, 4-tifluoromethylacetophenone, phenyl acetone, 4'-chlorophenyl acetone, 2'-hydroxyphenyl acetone, 3'-hydroxyphenyl acetone, 4'-hydroxyphenyl acetone, 2'-methoxyphenyl acetone, 3'-methoxyphenyl acetone, 4'-methoxyphenyl acetone, 2',4'-dimethoxyphenyl acetone, 3',4'-dimethoxyphenyl acetone, 2'-trifluoromethylphenyl acetone, 3'-trifuoromethylphenyl acetone, 4'-trifluoromethylphenyl acetone, 1-naphthyl acetone, 2-naphthyl acetone, 2-acetylpyridine, 3-acetylpyridine, 4-acetylpyridine, acetylpyrazine, 2-acetylfuran, 3-acetylfuran, 2-acetylthiophene, 3-acetylthiophene, 2-acetylthiazole, and the like.

In the above general formula (2), each of p, q, r, R and X includes the same groups as those of the general formula (1).

Concrete examples of the above compound represented by the general formula (2) mentioned above include, for instance, 4-chloro-α-phenethylamine, 2-hydroxy-α-phenethylamine, 3-hydroxy-α-phenethylamine, 4-hydroxy-α-phenethylamine, 2-methoxy-α-phenethylamine, 3-methoxy-α-phenethylamine, 4-methoxy-α-phenethylamine, 2,4-dimethoxy-α-phenethylamine, 3,4-dimethoxy-α-phenethylamine, 2-trifuoromethyl-α-phenethylamine, 3-trifluoromethyl-α-phenethylamine, 4-trifluoromethyl-α-phenethylamine, 1-phenyl-2-aminopropane, 1-(4-chlorophenyl)-2-aminopropane, 1-(2-hydroxyphenyl)-2-aminopropane, 1-(3-hydroxyphenyl)-2-aminopropane, 1-(4-hydroxyphenyl)-2-aminopropane, 1-(2-methoxyphenyl)-2-aminopropane, 1-(3-methoxyphenyl)-2-aminopropane, 1-(4-methoxyphenyl)-2-aminopropane, 1-(2,4-dimethoxyphenyl)-2-aminopropane, 1-(3,4-dimethoxyphenyl)-2-aminopropane, 1-(2-trifluoromethylphenyl)-2-aminopropane, 1-(3-trifluoromethylphenyl)-2-aminopropane, 1-(4-trifluoromethylphenyl)-2-aminopropane, 1-(1-naphthyl)-2-aminopropane, 1-(2-naphthyl)-2-aminopropane, 1-(2-pyridyl)ethylamine, 1-(3-pyridyl)ethylamine, 1-(4-pyridyl)ethylamine, 1-pyrazylethylamine, 1-(2-furyl)ethylamine, 1-(3-furyl)ethylamine, 1-(2-thienyl)ethylamine, 1-(3-thienyl)ethylamine, 1-(2-thiazoyl)ethylamine, and the like.

The amino group donor usable in the present invention includes a compound represented by the general formula (3):

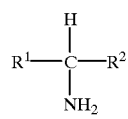

(3)

Such a compound encompasses achiral, optically active compounds and racemic modifications thereof.

In the above general formula (3), each of $R^1$ and $R^2$ is independently hydrogen atom; a substituted or unsubstituted alkyl group having 1 to 14 carbon atoms, preferably 1 to 4 carbon atoms, or a substituted or unsubstituted aryl group having 6 to 14 carbon atoms, preferably 6 to 10 carbon atoms.

Concrete examples of $R^1$ mentioned above include preferably an alkyl group having 1 to 10 carbon atoms, or phenyl group, and concrete examples of $R^2$ mentioned above include preferably hydrogen atom, methyl group and ethyl group.

Concrete examples of the above compound represented by the general formula (3) include α-phenethylamine, 2-butylamine, 2-pentylamine, 2-heptylamine, 2-octylamine and optically active modifications thereof.

In Process I, when the (S)-α-phenethylamine:pyruvate transaminase is allowed to act to the above ketone compound in the presence of an amino group donor, one or more kinds selected from the group consisting of a culture of a microorganism for producing the (S)-α-phenethylamine:pyruvate transaminase, isolated cells, immobilized cells and cell-free extracts may be used; or alternatively, one or more kinds selected from the group consisting of crudely purified enzymes, purified enzymes and immobilized enzymes of the (S)-α-phenethylamine:pyruvate transaminase may be used.

As to the concentrations of the substrate used in the reaction, it is preferable that the ketone compound is used at a concentration of 0.1 to 10% by weight, preferably 1 to 5% by weight, of the reaction mixture composition, and that the amino group donor, as in the case of a chiral amine, is used at a concentration of mainly (S) modification of 80 to 150% by mol to the ketone compound. Incidentally, a racemic modification of the amino compound can be also used as the amino group donor at a similar concentration.

It is desired that pH when the enzyme of the present invention is acted is preferably a pH of 6.0 or more, more preferably a pH of 7.0 or more, and that it is preferably a pH of 10.0 or less, more preferably a pH of 9.0 or less, from the viewpoint of the optimal pH of the enzyme.

The temperature when the enzyme of the present invention is acted is preferably 25° C. or more, more preferably 30° C. or more, and it is preferably 60° C. or less, more preferably 50° C. or less, from the viewpoints of the optimal temperature and the thermostability of the enzyme.

Process II

The enzyme of the present invention acts specifically on one of the configuration [(S)-modification] of the chiral amino compounds. Therefore, the (S)-α-phenethylamine:pyruvate transaminase of the present invention acts on a racemic modification of an amino compound represented by the general formula (4):

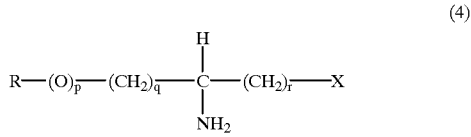

(4)

in the presence of an amino group receptor, to thereby only convert the amino compound of (S)-modification to the ketone compound. Therefore, an optically active amino compound of (R)-modification represented by the general formula (5):

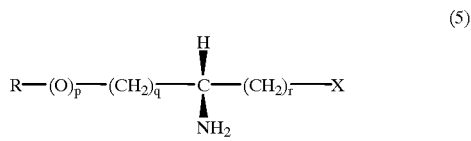

(5)

can be obtained.

In the above general formulas (4) and (5), each of R, p, q, r and X has the same groups as those of R, p, q, r and X in the above general formula (1).

The amino group receptor used in the present invention is not particularly limited, and concretely, there can be included pyruvic acid, glyoxylic acid, oxaloacetic acid and the like.

In Process II, when the (S)-α-phenethylamine:pyruvate transaminase is allowed to act on the racemic modification of an amino compound represented by the general formula (4) in the presence of an amino group receptor, one or more kinds selected from the group consisting of a culture of a microorganism for producing the (S)-α-phenethylamine:pyruvate transaminase, isolated cells, immobilized cells and cell-free extracts may be used; or alternatively, one or more kinds selected from the group consisting of crudely purified enzymes, purified enzymes and immobilized enzymes of the (S)-α-phenethylamine:pyruvate transaminase may be used.

As to the concentrations of the substrate used in the reaction, it is preferable that the racemic modification of an amino compound is used at a concentration of 0.1 to 20% by weight, preferably 1 to 10% by weight, of the reaction mixture composition. Also, it is preferable that the amino group receptor is used at a concentration of 30 to 100% by mol, preferably 50 to 60% by mol, to the racemic modification of the amino compound.

It is desired that pH when the enzyme of the present invention is acted is preferably a pH of 6.0 or more, more preferably a pH of 7.0 or more, and that it is preferably a pH of 10.0 or less, more preferably a pH of 9.0 or less, from the viewpoint of the optimal pH of the enzyme.

The temperature when the enzyme of the present invention is acted is preferably 25° C. or more, more preferably 30° C. or more, and it is preferably 60° C. or less, more preferably 50° C. or less, from the viewpoints of the optimal temperature and the thermostability of the enzyme.

The yield and the purity of the optically active amino compound prepared by these processes can be quantitatively analyzed, for instance, by separating the reaction mixture with a reverse-phase column ("COSMOSIL 5 $C_{18}$-AR," nacalaitesque, or the like) and 25% acetonitrile or the like as a mobile phase; and comparing absorbance at 210 nm with that of a control. In addition, as to a method for determining optical purity, the formed amino compound is bound to N-carboxy-L-leucine anhydride, or the like to form a diastereomer, and the optical purity can be determined by high-performance liquid chromatography by applying the resulting diastereomer to a reverse-phase column ("COSMOSIL 5 $C_{18}$-AR," nacalaitesque, or the like).

The present invention will be described more concretely hereinbelow by means of the working examples, without intending to restrict the scope of the present invention thereto.

EXAMPLE 1

Each 2 g of soil samples collected at various places in this country was suspended in 5 mL physiological saline. The 0.2 mL supernatant thereof was added to a 4 mL S-medium (2 g/L $KH_2PO_4$, 2 g/L $K_2HPO_4$, 0.3 g/L $MgSO_4.7H_2O$, 0.5 g/L glycerol, 3 g/L NaCl, 1 g/L yeast extract, 0.004 g/L $FeSO_4.7H_2O$, 0.0005 g/L $ZnSO_4.7H_2O$, 0.0005 g/L $MnCl_2.4H_2O$, pH 7.5, after a treatment of autoclaving; and thereafter adding 2-oxoglutaric acid or pyruvic acid and (S)-1-(3,4-dimethoxyphenyl)-2-aminopropane, each of which was filtrated by a microorganisms exclusion filter (manufactured by ADVANTEC under the trade name "DISMIC-25CS"), so as to give final concentrations of 1.5 g/L and 1.0 g/L, respectively. The resulting culture was subjected to an enrichment culture at 30° C. for 3 to 7 days. Each 0.2 mL culture in which the bacteria were grown was spread on an S-medium plate containing 1.5% agar, and cultured at 30° C. for 72 hours. The grown colonies were cultured with shaking in the S-medium for each of the bacterial cells (30° C., 24 hours) to harvest the cells. Subsequently, the resulting bacterial cells were suspended in a 0.25 mL solution containing 0.1 M carbonate buffer (pH 8.5), 50 mM pyruvic acid and 30 mM (S)-1-(3,4-dimethoxyphenyl)-2-aminopropane. The resulting suspension of the bacterial cells was reacted at 30° C. for 24 hours with stirring.

The reaction mixture obtained after termination of reaction was separated by thin-layer chromatography [Kieselgel 60F254 (manufactured by Merck); developing solvent being diethyl ether:methanol:aqueous ammonia solution (27%)= 50:50:2]. Thereafter, the formation of the resulting product, 1-(3,4-dimethoxyphenyl)-2-propanone, was detected by 0.4% 2,4-dihydrophenyl hydrazine. With regard to the strains in which the formation of 1-(3,4-dimethoxyphenyl)-2-propanone was confirmed, the bacterial cells cultured in the above S-medium at 30° C. for 24 hours were suspended in a solution containing 0.6% 1-(3,4-dimethoxyphenyl)-2-propanone and an amino group donor, 0.6% (S)-α-phenylethylamine. Thereafter, the resulting reaction mixture was reacted at 30° C. for 2 days with stirring. As a result, there were found that the Pseudomonas species KNK425 strain had the (S)-selective transamination activity.

EXAMPLE 2

Pseudomonas species KNK425 isolated from the soil was inoculated to a 50 mL medium (composition: 5 g/L $KH_2PO_4$, 5 g/L $K_2HPO_4$, 1 g/L $MgSO_4.7H_2O$, 0.005 g/L $ZnSO_4.7H_2O$, 0.005 g/L $FeSO_4.7H_2O$, 0.001 g/L $MnCl_2.4H_2O$, 3 g/L NaCl, 15 g/L glycerol, 2 g/L yeast extract, 8 g/L proextract, 2 g/L (RS)-2-butylamine, 1.5 g/L pyruvic acid, pH 7.2) in a 500-mL Sakaguchi flask, and cultured at 30° C. for 1 day, to give a preculture. Thereafter, the resulting preculture was inoculated to a 3.0-liter medium (the same composition as the medium mentioned above) in a 5-liter mini jar, and cultured at 30° C. for 22 hours under conditions of 0.5 vvm, 600 rpm and a pH of 7.5 or less.

Subsequently, the bacterial cells were harvested from the resulting culture by centrifugation, and the cells were suspended in 320 mL of 0.05M potassium phosphate buffer (pH 6.8) containing 0.1% 2-mercaptoethanol and 0.1 mM pyridoxal phosphate.

The resulting suspension of the bacterial cells was disrupted by DYNOMILL, and thereafter supernatant was obtained by centrifugation (enzyme specific activity: 0.57 U/mg).

The resulting supernatant was heat-treated at 50° C. for 30 minutes, and thereafter the precipitate was removed by centrifugation. Five milliliters of sulfate protamine (1 g/20 mL) was added to the resulting supernatant to remove a nucleic acid (enzyme specific activity: 0.93 U/mg).

The resulting sulfate protamine-treated solution was charged to DEAE-Sepharose Fast Flow (Pharmacia LKB) column (column diameter: 4.0 cm, height 18 cm) previously equilibrated with 0.05M potassium phosphate buffer (pH 6.8) containing 0.01% 2-mercaptoethanol and 20 μM pyridoxal phosphate, and eluted at a flow rate of 40 mL/hr on a 0–0.2M NaCl linear concentration gradient, to collect an active fraction. The resulting active fraction was dialyzed against 2 L of 0.05M potassium phosphate buffer (pH 6.8) containing 0.01% 2-mercaptoethanol and 20 μM pyridoxal phosphate. Thereafter, the resulting dialyzed solution was charged to Q-Sepharose (Pharmacia LKB) column (column diameter: 2.4 cm, height 17 cm) previously equilibrated with 0.05M potassium phosphate buffer (pH 6.8) containing 0.01% 2-mercaptoethanol and 20 μM pyridoxal phosphate, and eluted at a flow rate of 40 mL/hr on a 0–0.25M NaCl linear concentration gradient, to collect an active fraction (enzyme specific activity: 8.37 U/mg).

The resulting active fraction was charged to Phenyl-Sepharose Fast Flow column (column diameter: 1.4 cm, height: 15 cm) previously equilibrated with 0.05M potassium phosphate buffer (pH 6.8) containing 0.01% 2-mercaptoethanol and 20 μM pyridoxal phosphate, and eluted at a flow rate of 30 mL/hr on a stepwise concentration gradient of 5%, 10% and 30% ethylene glycol, to collect an active fraction (enzyme specific activity: 16.49 U/mg).

The resulting active fraction was subjected to SDS-polyacrylamide gel electrophoresis, and as a result, a single band was formed at a position corresponding to a molecular weight of about 44,000.

EXAMPLE 3

The physiochemical properties for the purified enzyme obtained in Example 2 were examined.
(Action)

The enzyme acted on (S)-α-phethylamine and pyruvic acid, to thereby respectively form acetophenone and alanine.
(Optimal pH)

The (S)-α-phethylamine pyruvate transaminase activity was assayed in a pH range of 5 to 10 by using 0.1M phosphate buffer and 0.1M Tris-hydrochloric acid buffer. The results thereof are shown in FIG. 1. The optimal pH was 7.0 to 9.0.
(Optimal Temperature)

The (S)-α-phethylamine:pyruvate transaminase activity was assayed in a temperature range of 20° to 70° C. by using 0.05M potassium phosphate buffer (pH 6.8) as a buffer. The results thereof are shown in FIG. 2. The optimal temperature was 30° to 50° C.
(Thermostability)

Figure 3:
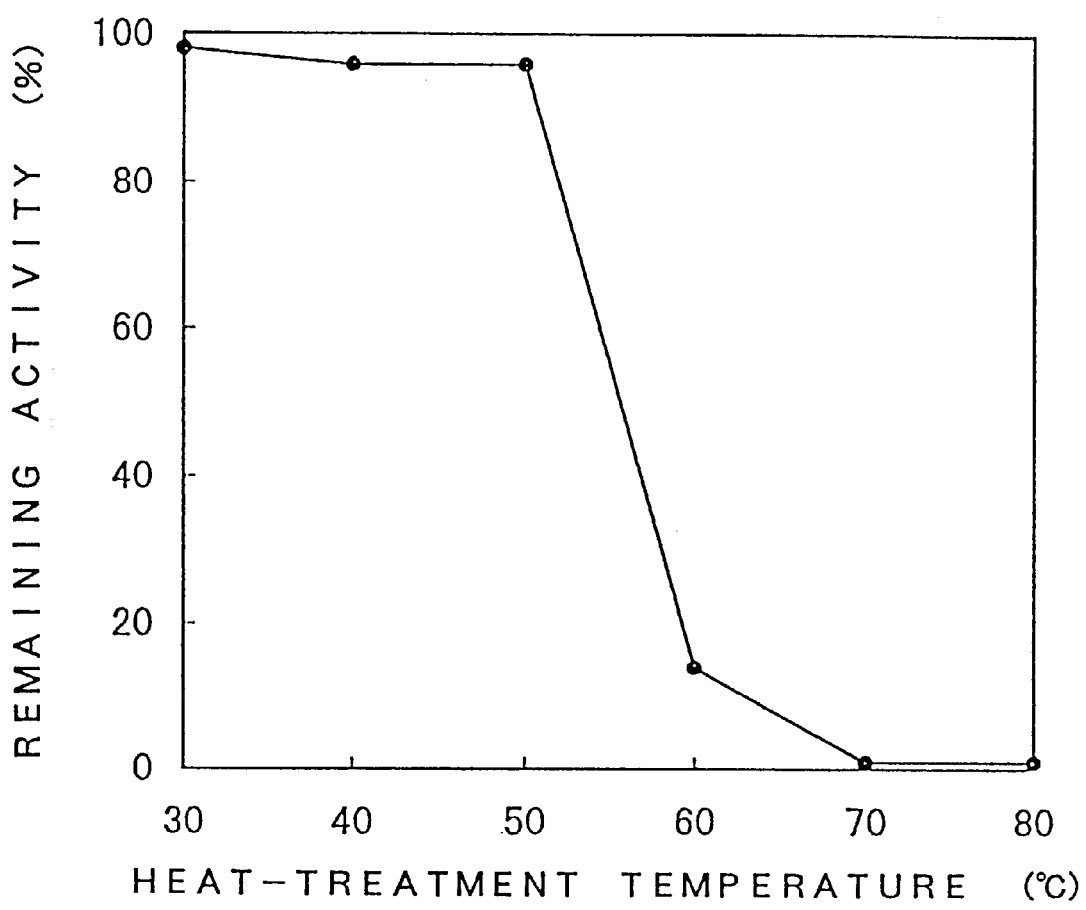
FIG. 3 is a graph showing thermostability of (S)-α-phenethylamine:pyruvate transaminase.

The (S)-α-phethylamine:pyruvate transaminase activity was assayed after a treatment at 30° to 80° C. for 15 minutes in 0.05M potassium phosphate buffer (pH 7.0). The results thereof are shown in FIG. 3. As compared to the entire activity before treatment, 95% or more of the activity remained at 30° to 50° C.
(N-Terminal Sequence)

The amino acid sequence was examined by analyzing the purified enzyme protein with a vapor phase protein sequencer [492 PROTEIN SEQUENCER (Applied Biosystems)]. As a result, it was shown that the enzyme had the amino acid sequence as shown in SEQ ID NO: 1 as an N-terminal amino acid sequence.

EXAMPLE 4

Using the purified enzyme solution obtained in Example 2, the substrate specificity of this enzyme for each of the amino group donors was examined.

To 0.9 mL of 0.1M potassium phosphate solution (pH 7.0) containing 22.5 mM of various amino compounds, 22.5 mM pyruvic acid, and 0.1 mM pyridoxal phosphate was added 0.1 mL of the purified enzyme. The mixture was reacted at 30° C. for 1 hour, and thereafter immersed in boiling water for 5 minutes, to stop the reaction. The reaction mixture obtained after termination of reaction was diluted five times with 0.2M sodium carbonate buffer, and 0.2 mL of a 10 mM acetone solution of dabsyl chloride was added to 0.1 mL portion of the resulting dilution. The reaction mixture was reacted at 70° C. for 15 minutes, and after cooling, 0.1 mL of 1 N HCl was added. This reaction mixture was analyzed by high-performance liquid chromatography to quantify dabsylated alanine.

The assay conditions by high-performance liquid chromatography are as follows.

| Column: | Deverosil ODS-HG-3 (NOMURA CHEMICAL) |
|---|---|
| Eluent: | Acetonitrile/0.045 M acetate buffer (pH 4.13) = 35/65 (volume ratio) |
| Flow Rate: | 1 mL/minute |
| Detection: | 436 nm |

The results thereof, expressed in terms of the relative activity where an activity when using (S)-phenethylamine as an amino group donor is 100, are shown in Table 2.

TABLE 2

| Amino Group Donor | Relative Activity (%) |
|---|---|
| n-Propylamine | 0 |
| n-Butylamine | 2 |
| Amylamine | 5 |
| Cyclohexylamine | 1 |
| Benzylamine | 13 |
| β-Phenethylamine | 23 |
| 3-Phenylpropylamine | 1 |
| Isopropylamine | 0 |
| 2-Butylamine | 1 |
| 2-Pentylamine | 4 |
| 2-Heptylamine | 28 |
| 2-Octylamine | 46 |
| (R)-α-Phenethylamine | 3 |
| (S)-α-Phenethylamine | 100 |
| 3'-Hydroxy-α-phenethylamine | 52 |
| 1-(3,4-Dimethoxyphenyl)-2-aminopropane | 18 |
| 1-Phenyl-3-aminobutane | 80 |

As shown in Table 2, this enzyme exhibited an especially high activity for (S)-α-phenethylamine.

EXAMPLE 5

Using the purified enzyme solution obtained in Example 2, the substrate specificity of this enzyme for each of the amino group receptors was examined.

To 0.9 mL of 0.1M potassium phosphate solution (pH 7.0) containing 22.5 mM (S)-α-phenethylamine, 22.5 mM of various ketone compounds which were listed below, and 0.1 mM pyridoxal phosphate was added 0.1 mL of the purified enzyme. The mixture was reacted at 30° C. for 1 hour. The resulting reaction mixture was analyzed by high-performance liquid chromatography, to quantify acetophenone.

The assay conditions by high-performance liquid chromatography are as follows.

| Column: | Deverosil ODS-HG-3 (NOMURA CHEMICAL) |
|---|---|
| Eluent: | 750 mL of acetonitrile/2250 mL of distilled water/6.75 g of $KH_2PO_4$/2.7 g of $H_3PO_4$ |
| Flow Rate: | 1 mL/minute |
| Detection: | 210 nm |

The results thereof, expressed in terms of the relative activity where an activity when using pyruvic acid as an amino group receptor is 100, are shown in Table 3.

TABLE 3

| Amino Group Receptor | Relative Activity (%) |
|---|---|
| Pyruvic acid | 100 |
| 2-Ketoglutaric acid | 0 |
| Glyoxylic acid | 100 |
| 2-Ketobutyric acid | 5.8 |
| 2-Keto-valeric acid | 1.5 |

As shown in Table 3, this enzyme exhibited a high activity for pyruvic acid and glyoxylic acid, but did not exhibit an activity for 2-ketoglutaric acid.

EXAMPLE 6

Using the purified enzyme obtained in Example 2, the reactivity of the present enzyme for each of substrates of the representative ω-amino acid transaminases was evaluated in the same manner as in Example 4. The results thereof are shown in Table 4.

TABLE 4

| Amino Group Donor | Amino Group Receptor | Relative Activity (%) of (S)-α-Phenethyl-amine: Pyruvate Transaminase [Present Invention] | Relative Activity (%) of ω-Amino acid: Pyruvate Transaminase [Derived from Pseudomonas F-126] | Relative Activity (%) of 4-Amino-butyrate: 2-ketoglutarate Transaminase [Derived from Pseudomonas F-126] |
|---|---|---|---|---|
| (S)-α-Phenethyl-amine | Pyruvic acid | 100 | — | — |
| β-Alanine | Pyruvic acid | 0 | 100 | — |
| Taurine | Pyruvic acid | 0 | 132 | — |
| Putrescine | Pyruvic acid | 0 | 18 | — |
| B-Alanine | 2-Keto-glutaric acid | 0 | — | 0 |
| 4-Amino-butyric acid | 2-Keto-glutaric acid | 0 | — | 100 |
| Putrescine | 2-Keto-glutaric acid | 0 | — | 8 |

As shown in Table 4, the present enzyme exhibits a specifically high activity for (S)-α-phenethylamine, but does not act on substrates of the 5 representative ω-amino acid transaminases, the substrates including β-alanine, taurine, putrescine, 4-aminobutyric acid, and the like.

EXAMPLE 7

Using the purified enzyme obtained in Example 2, the activity for each of various ketone compounds when (S)-α-phenethylamine was used as an amino group donor was evaluated in the same manner as in Example 5. The results thereof are shown in Table 5.

TABLE 5

| Amino Group Receptor | Relative Activity (%) |
|---|---|
| 3'-Methoxyacetophenone | 4 |
| 2'-Hydroxyacetophenone | 24 |
| 3'-Hydroxyacetophenone | 6 |
| 4'-Chloroacetophenone | 22 |
| 4'-Methoxyphenyl acetone | 12 |
| 3',4'-Dimethoxyphenyl acetone | 38 |
| 3'-Trifluoromethylphenyl acetone | 60 |
| Benzyl acetone | 70 |
| 4-(4'-Methoxyphenyl)-2-butanone | 35 |
| 1-Phenyl-2-butanone | 5 |
| Benzoyl acetone | 12 |
| 2-Acetylpyridine | 42 |
| 3-Acetylpyridine | 14 |
| 4-Acetylpyridine | 8 |
| Acetylpyrazine | 100 |
| 2-Acetylfuran | 3 |
| 2-Acetylthiazole | 4 |

It is found that when (S)-α-phenethylamine was used as an amino group donor, activities were exhibited for various compounds as shown in Table 5.

EXAMPLE 8

Using the purified enzyme obtained in Example 2, the activity for each of various ketone compounds other than those used in Example 7, when (S)-α-phenethylamine was used as an amino group donor, was evaluated in the same manner as in Example 5. The results thereof are shown in Table 6.

TABLE 6

| Amino Group Receptor | Relative Activity (%) |
|---|---|
| Pyruvic acid | 100 |
| Phenylacetaldehyde | 37 |
| 3-Phenylpropionaldehyde | 16 |
| Phenoxy-2-propanone | 46 |
| Methoxypropanone | 5 |

As shown in Table 6, the enzyme exhibits a high activity for pyruvic acid.

EXAMPLE 9

Two milliliters of 0.1M potassium phosphate buffer (pH 7.5) containing 2 units of the purified enzyme, 10 mg of (S)-α-phenethylamine and 10 mg of 3-hydroxyacetophenone was reacted at 30° C. for 24 hours with stirring. After the termination of reaction, the resulting reaction mixture was analyzed by high-performance liquid chromatography. As a result, 7 mg of (S)-3-hydroxy-α-phenethylamine was formed. Its optical purity was 99 e.e. % or more.

$^1$H-NMR (400 Mz, CDCl$_3$): δ=1.39–1.40 (d, 3H), 2.72 (bs, 2H), 4.05–4.10 (q, 1H), 6.70–7.19 (4H)

EXAMPLE 10

Two milliliters of 0.1M phosphate buffer (pH 7.5) containing 1 unit of the purified enzyme, 10 mg of (S)-α-phenethylamine, and 10 mg of 3'-trifluoromethylphenyl acetone were reacted at 30° C. for 24 hours with stirring. After the termination of reaction, the resulting reaction mixture was analyzed by high-performance liquid chromatography. As a result, 8.5 mg of (S)-1-(3-trifluoromethylphenyl)-2-aminopropane was formed. Its optical purity was 99 e.e. % or more.

EXAMPLE 11

Pseudomonas species KNK425 strain was cultured in a 100 mL medium (composition: 5 g/L KH$_2$PO$_4$, 5 g/L K$_2$HPO$_4$, 1 g/L MgSO$_4$.7H$_2$O, 0.005 g/L ZnSO$_4$.7H$_2$O, 0.005 g/L FeSO$_4$.7H$_2$O, 0.001 g/L MnCl$_2$.4H$_2$O, 3 g/L NaCl, 15 g/L glycerol, 2 g/L yeast extract, 8 g/L proextract, 2 g/L (RS)-2-butylamine, 1.5 g/L pyruvic acid, pH 7.2) for 20 hours. After 50 mL of this culture was centrifuged, the precipitated bacterial cells were suspended in 50 mL of 50 mM phosphate buffer (pH 6.8) containing 0.1% 2-mercaptoethanol and 0.1 mM pyridoxal phosphate. This suspension was ultrasonically disrupted on ice ("BRANSON SONIFIER 250," Duty Cycle 7, Outputcontrole 7, 2 minutes, 12 runs). The disrupted bacterial cell solution obtained in the manner described above had 4 U/mL of (S)-α-phenethylamine:pyruvate transaminase activity.

EXAMPLE 12

One gram of (S)-α-phenethylamine and 1 g of 3-hydroxyacetophenone were added to 100 mL of a culture of Pseudomonas species KNK425 cultured in the same manner as in Example 11, and pH was adjusted to 7.5 using hydrochloric acid. The mixture was reacted at 37° C. for 24 hours with stirring. The reaction mixture obtained after the termination of reaction was analyzed by high-performance liquid chromatography. As a result, 75% of 3-hydroxyacetophenone was converted to (S)-3-hydroxy-α-phenethylamine. pH Of the reaction mixture was adjusted to 2.0 using hydrochloric acid, and the reaction mixture was extracted with toluene, to remove the ketones in the organic layer. Thereafter, pH of the aqueous layer was adjusted to 10.0 using an aqueous sodium hydroxide, and thereafter extracted again with toluene. As a result, the organic layer contained 0.7 g of (S)-3-hydroxy-α-phenethylamine. The resulting extract was evaporated to a dry solid, and thereafter recrystallized from a mixture of ethanol:water=1:1, to give 0.65 g of (S)-3-hydroxy-α-phenethylamine as crystals. The resulting (S)-3-hydroxy-α-phenethylamine had an optical purity of 99 e.e. % or more.

EXAMPLE 13

Twenty milligrams of 2-butylamine and 20 mg of 3-trifluoromethylphenyl acetone were added to 2 mL of a culture of Pseudomonas species KNK425 cultured in the same manner as in Example 11, and pH was adjusted to 7.5 using hydrochloric acid. The mixture was reacted at 40° C. for 24 hours with stirring. The reaction mixture obtained after termination of reaction was analyzed by high-performance liquid chromatography. As a result, 50% of 3'-trifluoromethylphenyl acetone was converted to (S)-3'-trifluoromethylphenyl-2-aminopropane. The resulting (S)-3'-trifluoromethylphenyl-2-aminopropane had an optical purity of 99% e.e. or more.

$^1$H-NMR (400 Mz, CDCl$_3$): σ=1.12–1.13 (d, 3H), 1.57 (bs, 2H), 2.58–2.63 (dd, 1H), 2.73–2.78 (dd, 1H), 3.16–3.24 (m, 1H), 7.37–7.48 (4H)

EXAMPLE 14

Forty milligrams of (S)-α-phenethylamine and 40 mg of 3'-trifluoromethylphenyl acetone were added to 2 mL of a culture of Pseudomonas species KNK425 cultured in the same manner as in Example 11, and pH was adjusted to 7.5 using hydrochloric acid. Thereafter, the mixture was reacted at 40° C. for 24 hours with stirring. The reaction mixture obtained after the termination of reaction was analyzed by high-performance liquid chromatography. As a result, 80% of 3'-trifuoromethylphenyl acetone was converted to (S)-3-trifluoromethylphenyl-2-aminopropane. The resulting (S)-3-trifluoromethylphenyl-2-aminopropane had an optical purity of 99% e.e. or more.

EXAMPLE 15

The supernatant of 50 mL of a culture of Pseudomonas species KNK425 cultured in the same manner as in Example 11 was centrifuged to thereby remove supernatant. The precipitated bacterial cells were suspended in 20 mL of 0.1 M potassium phosphate buffer (pH 6.8), and the bacterial cells were ultrasonically disrupted. The resulting disrupted products were centrifuged to thereby remove the precipitates, to give 17 mL of a cell-free extract. To 17 mL of the cell-free extract were added 0.2 g of (S)-α-phenethylamine and 0.2 g of 3'-trifluoromethylphenyl acetone. Subsequently, pH of the mixture was adjusted to 7.5 using hydrochloric acid, and thereafter the reaction mixture was reacted at 40° C. for 24 hours. As a result, 0.6 g of (S)-3'-trifluoromethylphenyl-2-aminopropane was formed. The optical purity of the resulting (S)-3'-trifluoromethylphenyl-2-aminopropane was 99% e.e. or more.

EXAMPLE 16

Sixty milligrams of a racemic modification of α-phenethylamine and 30 mg of pyruvic acid were added to 2 mL of a culture of Pseudomonas species KNK425 cultured in the same manner as in Example 11, and pH of the mixture was adjusted to 7.5 using an aqueous sodium hydroxide. Thereafter, the mixture was reacted at 40° C. for 25 hours. As a result, 27 mg of α-phenethylamine remained, and the optical purity of its (R) modification was 99% e.e. or more.

EXAMPLE 17

Sixty milligrams of a racemic modification of 3-hydroxy-α-phenethylamine and 30 mg of pyruvic acid were added to 2 mL of a culture of Pseudomonas species KNK425 cultured in the same manner as in Example 11, and pH of the mixture was adjusted to 7.5 using an aqueous sodium hydroxide. Thereafter, the resulting solution was reacted at 40° C. for 25 hours. As a result, 27 mg of 3-hydroxy-α-phenethylamine remained, and the optical purity of its (R) modification was 99% e.e. or more.

EXAMPLE 18

The same procedures as in Example 17 were carried out except for using glyoxylic acid in place of pyruvic acid, whereby 26 mg of 3-hydroxy-α-phenethylamine remained, and the optical purity of its (R) modification was 99% e.e. or more.

EXAMPLE 19

The same procedures as in Example 17 were carried out except for using oxaloacetic acid in place of pyruvic acid, whereby 27 mg of 3-hydroxy-α-phenethylamine remained, and the optical purity of its (R) modification was 99% e.e. or more.

INDUSTRIAL APPLICABILITY

According to the (S)-α-phenethylamine:pyruvate transaminase of the present invention, a ketone compound can be efficiently converted to an optically active amino compound. According to the process for preparing the optically active amino compound of the present invention, an optically active amino compound can be obtained in a high yield. Moreover, since the optical purity of the resulting optically active amino compound is high, the process is useful in the preparation of pharmaceuticals and agricultural chemicals.

What is claimed is:

1. An isolated (S)-α-phenethylamine:pyruvate transaminase having the following physicochemical properties:

(A): action:
   acting on optically active (S)-α-phenethylamine and pyruvic acid, thereby catalyzing transamination for forming acetophenone and alanine, respectively; and (B): substrate specificity:
   (a) amino group donor: exhibiting activity to (S)-α-phenethylamine but not exhibiting activity to each of β-alanine, taurine, putrescine, DL-ornithine and DL-lysine; and
   (b) amino group receptor: exhibiting activity to pyruvic acid and glyoxylic acid.

2. The (S)-α-phenethylamine:pyruvate transaminase according to claim 1, which acts on (S)-α-phenethylamine and a ketone compound other than an α-keto-acid, thereby catalyzing transamination for forming acetophenone and an amino compound corresponding to the ketone compound.

3. The (S)-α-phenethylamine:pyruvate transaminase according to claim 2, wherein the ketone compound is a ketone compound represented by the general formula (1):

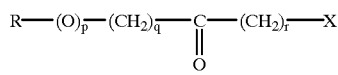

(1)

wherein p is 0 or 1; q is an integer of 0 to 8; r is an integer of 0 to 4; R is a substituted or unsubstituted aryl group having 6 to 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkoxycarbonyl group having 2 to 6 carbon atoms, or hydrogen atom.

4. The (S)-α-phenethylamine:pyruvate transaminase according to claim 2 or 3, wherein the ketone compound is at least one kind selected from the group consisting of 3-methoxyacetophenone, 2-hydroxyacetophenone, 3-hydroxyacetophenone, 4-chloroacetophenone, 4'-methoxyacetophenone, 3',4'-dimethoxyphenyl acetone, 3'-trifluoromethyl acetone, benzyl acetone, 4-(4'-methoxyphenyl)-2-butanone, benzoyl acetone, 2-acetylpyridine, acetylpyridine, 2-acetylfuran and 2-acetylthiazole.

5. The (S)-α-phenethylamine:pyruvate transaminase according to claim 4, capable of acting on (S)-α-phenethylamine and 3-hydroxyacetophenone, thereby forming acetophenone and an optically active (S)-3-α-hydroxyphenethylamine.

6. The (S)-α-phenethylamine:pyruvate transaminase according to claim 1, having the following physicochemical properties:

a) molecular weight: about 44,000 (SDS-PAGE);
   b) optimal pH: 7.0 to 9.0;
   c) optimal temperature: 30° to 50° C.; and
   d) thermostability: retaining a remaining activity of 95% or more of a total activity before treatment, when treated at pH 7.0 and a temperature of 30° to 50° C. for 15 minutes.

7. The (S)-α-phenethylamine:pyruvate transaminase according to claim 1, having the amino acid sequence as shown in SEQ ID NO: 1 as an N-terminal amino acid sequence.

8. The (S)-α-phenethylamine:pyruvate transaminase according to claim 1, produced by a microorganism of the genus Pseudomonas.

9. The (S)-α-phenethylamine:pyruvate transaminase according to claim 8, wherein the microorganism belonging to the genus Pseudomonas is Pseudomonas sp. KNK425 (FERM BP-6525).

10. A process for preparing an optically active amino compound, comprising acting the (S)-α-phenethylamine:pyruvate transaminase on a ketone compound represented by the following general formula (1):

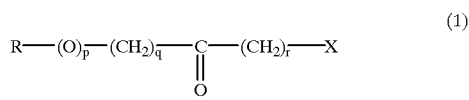

(1)

wherein p is 0 or 1; q is an integer of 0 to 8; r is an integer of 0 to 4; R is a substituted or unsubstituted aryl group having 6 to 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkoxycarbonyl group having 2 to 6 carbon atoms or hydrogen atom, in the presence of an amino group donor, to thereby give an optically active amino compound having the configuration represented by the general formula (2):

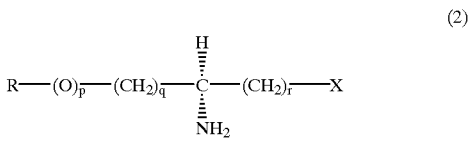

(2)

wherein each of p, q, r, R and X has the same definitions as those of p, q, r, R and X in the general formula (1).

11. The process according to claim 10, wherein in the general formulas (1) and (2), R is an aryl group substituted in at least one site by a substituent selected from the group consisting of a halogen atom, an alkyl group having 1 to 6 carbon atoms, hydroxyl group, methoxy group, nitro group, monofluoromethyl group, difluoromethyl group and trifluoromethyl group.

12. The process according to claim 11, wherein in the general formulas (1) and (2), R is methyl group, phenyl group, naphthyl group, 2-chlorophenyl group, 3-chlorophenyl group, 4-chlorophenyl group, 2-hydroxyphenyl group, 3-hydroxyphenyl group, 4-hydroxyphenyl group, 2-methoxyphenyl group, 3-methoxyphenyl group, 4-methoxyphenyl group, 2,4-dimethoxyphenyl group, 3,4-dimethoxyphenyl group, 2-trifluoromethylphenyl group, 3-trifluoromethylphenyl group, 4-trifluoromethylphenyl group, pyridyl group, pyrazinyl group, pyrrolyl group, thienyl group, furyl group, or thiazolyl group.

13. The process according to any one of claims 10 to 12, wherein in the general formulas (1) and (2), each of p and q is 0, r is 1, and X is hydrogen atom.

14. The process according to any one of claim 10, wherein in the general formulas (1) and (2), p is 0, q is 1, r is 1, and X is hydrogen atom.

15. The process according to any one of claim 10, wherein the amino group donor is a compound represented by the general formula (3):

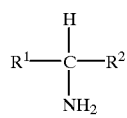

(3)

wherein each of $R_1$ and $R_2$ is independently hydrogen atom, a substituted or unsubstituted alkyl group having 1 to 14 carbon atoms, or a substituted or unsubstituted aryl group having 6 to 14 carbon atoms.

16. The process according to claim 15, wherein in the general formula (3), $R^1$ is an alkyl group having 1 to 10 carbon atoms or phenyl group, and $R^2$ is hydrogen atom, methyl group or ethyl group.

17. The process according to claim 15 or 16, wherein the amino group donor is a compound selected from the group consisting of α-phenethylamine, 2-butylamine, 2-pentylamine, 2-heptylamine, 2-octylamine and optically active substances thereof.

18. The process according to any one of claim 10, wherein one or more members selected from the group consisting of a culture of a microorganism for producing the (S)-α-phenethylamine:pyruvate transaminase, isolated cells, immobilized cells and cell-free extracts are used when the (S)-α-phenethylamine:pyruvate transaminase is allowed to act.

19. The process according to any one of claim 10, wherein one or more members selected from the group consisting of crudely purified enzymes, purified enzymes and immobilized enzymes of the (S)-α-phenethylamine pyruvate transaminase are used, when the (S)-α-phenethylamine pyruvate transaminase is allowed to act.

20. A process for preparing an optically active amino compound, comprising acting a (S)-α-phenethylamine: pyruvate transaminase having the following physiochemical properties:

(A) action:
acting on optically active (S)-α-phenethylamine and pyruvic acid, thereby catalizing transamination for forming acetophenone and alanine, respectively; and (B) substrate specificity;
(a) amino group donor: exhibiting activity to (S)-α-phenethylamine but not exhibiting activity to each of β-alanine, taurine, putrescine, DL-ornithine and DL-lysine; and
(b) amino group receptor: exhibiting activity to pyruvic acid and glyoxylic acid, pyruvic acid and glyoxylic acid, on a racemic modification of an amino compound represented by the general formula (4):

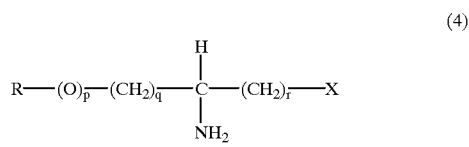

(4)

wherein p is 0 or 1; q is an integer of 0 to 4; R is a substituted or unsubstituted aryl group having 6 14 carbon atoms, a heterocyclic group having 4 to 12 carbon atoms, carboxyl group, an alkoxycarbonyl group having 2 to 6 carbon atoms, methyl group or hydrogen atom; and X is hydroxyl group, carboxyl group, an alkocarbonoxyl group having 2 to 6 carbon atoms or hydrogen atom, in the presence of an amino group receptor, to thereby give an optically active amino compound having the configuration represented by the general formula (5):

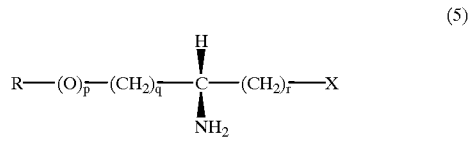

(5)

wherein each of p, q, r, R and X has the same groups as those of p, q, r, R and X in the general formula (4).

21. The process according to claim 20, wherein the amino group receptor is a compound selected from pyruvic acid, glyoxylic acid and oxaloacetic acid.

22. The process according to claim 20 or 21, wherein one or more members selected from the group consisting of a culture of a microorganism for producing the (S)-α-phenethylamine:pyruvate transaminase, isolated cells, immobilized cells, and cell-free extracts are used when the (S)-α-phenethylamine:pyruvate transaminase is allowed to act.

23. The process according to claim 20 or 21, wherein one or more members selected from the group consisting of crudely purified enzymes, purified enzymes and immobilized enzymes of the (S)-α-phenethylamine:pyruvate transaminase are used when the (S)-α-phenethylamine:pyruvate transaminase is allowed to act.

24. A method for culturing a microorganism for producing the (S)-α-phenethylamine:pyruvate transaminase, comprising adding to a medium one or more compounds selected from the group consisting of propylamine, 1-butylamine, 2-butylamine, 2-pentylamine, isopropylamine and isobutylamine as an inducer for the enzyme when a microorganism for producing (S)-α-phenethylamine: pyruvate transaminase is cultured.

* * * * *